United States Patent [19]

Orvik et al.

[11] Patent Number: 5,480,991

[45] Date of Patent: Jan. 2, 1996

[54] 2-ALKOXY-4-HYDROAZINOPYRIMIDINE COMPOUNDS AND THEIR USE IN THE PREPARATION OF 5-ALKOXY-1,2,4-TRIAZOLO[4,3-C]PYRIMIDINE-3(2H)-THIONE COMPOUNDS

[75] Inventors: Jon A. Orvik, Midland; Dawn Shiang, Sanford, both of Mich.

[73] Assignee: DowElanco, Indianapolis, Ind.

[21] Appl. No.: 148,789

[22] Filed: Nov. 5, 1993

[51] Int. Cl.$^6$ .................................................. C07D 471/02

[52] U.S. Cl. ............................................................ 544/263

[58] Field of Search ............................ 544/263; 504/241

[56] References Cited

U.S. PATENT DOCUMENTS

| | | | |
|---|---|---|---|
| 4,528,288 | 7/1985 | Wade | 544/263 |
| 5,163,995 | 11/1992 | Van Heertum et al. | 544/263 |

FOREIGN PATENT DOCUMENTS

| | | | |
|---|---|---|---|
| 951652 | 3/1964 | United Kingdom | 544/263 |

OTHER PUBLICATIONS

Brown et al., *Australian Journal of Chemistry*, 31, 2505–2515 (1978).
Brown et al., *Australian Journal of Chemistry*, 32, 2713–2726, (1979).
Danagulyan et al., *Khimiya Geterotsiklicheskikh Soedinenii*, 2, 225–227 (1992).
Broadbent et al., *J. Chem. Soc.*, 1965, 3369–3372.
Miller et al., *J. Chem. Soc.*, 1963, 5642–5659.

*Primary Examiner*—Donald G. Daus
*Attorney, Agent, or Firm*—D. Wendell Osborne

[57] ABSTRACT

5-Alkoxy[1,2,4]triazolo[1,5-c]pyrimidine-2 (3H)-thione compounds, such as 5-ethoxy-8-fluoro[1,2,4] triazolo[1,5-c]pyrimidine-2(3H)-thione, were prepared by treatment of a 5-alkoxy-1,2,4-triazolo-[4,3-c] pyrimidine-3(2H)-thione compound, such as 5-ethoxy-8-fluoro-1,2,4-triazolo[4,3-c] pyrimidine-3(2H)-thione, with an alkali metal alkoxide in an alcohol solvent selected so that the 5-alkoxy group, the alkoxide, and the alcohol all have the same alkyl group. The trialkylammonium salts of the 5-alkoxy-1,2,4-triazolo [4,3-c]pyrimidine-3(2H)-thione compounds were converted to 3-hydrocarbylthio-5-alkoxy-1,2,4-triazolo-[4,3-c] pyrimidine compounds by reaction with a hydrocarbyl halide, such as benzyl chloride. The products are useful intermediates in the preparation of 5-alkoxy[1,2,4]triazolo[1,5-c]pyrimidine-2-sulfonamide herbicides.

23 Claims, No Drawings

2-ALKOXY-4-HYDROAZINOPYRIMIDINE COMPOUNDS AND THEIR USE IN THE PREPARATION OF 5-ALKOXY-1,2,4-TRIAZOLO[4,3-C] PYRIMIDINE-3(2H)-THIONE COMPOUNDS

BACKGROUND OF THE INVENTION

The present invention relates to 5-alkoxy- 1,2,4-triazolo [4,3-c]pyrimidine-3(2H)-thione compounds and to their use in the preparation of 5-alkoxy[1,2,4]-triazolo[1,5-c]pyrimidine-2(3H)-thione compounds and 3-hydrocarbylthio-5-alkoxy-1,2,4-triazolo[4,3-c]pyrimidine compounds. It further relates to the use of 3-hydrocarbylthio-5-alkoxy-1,2,4-triazolo[4,3-c]pyrimidine compounds for the preparation of 2-hydrocarbylthio- 5-alkoxy[1,2,4]triazolo[1,5-c]pyrimidine compounds.

5-Alkoxy[1,2,4]triazolo[1,5-c]pyrimidine-2-sulfonamide compounds that are potent herbicides are described in U.S. Pat. No. 5,163,995 and are disclosed to be prepared in a multistep process that utilizes appropriately substituted 2-hydrocarbylthio-5-alkylthio-1,2,4-triazolo[4,3-c]pyrimidine compounds as intermediates. The preparation requires a substitution reaction wherein the alkylthio moiety is replaced with an alkoxy moiety in the presence of an ethylenically unsubstituted compound capable of reacting with and removing the displaced alkanethiol. This process is lengthy, produces the desired products in only moderate yield, and results in a alkylthioethyl moiety-containing compound by-product which must be disposed of as waste. Improved methods of preparing herbicidal 5-alkoxy[1,2,4] triazolo[ 1,5-c]pyrimidine-2-sulfonamide compounds, including improved methods for preparing intermediates that are useful in their preparation, would be of considerable value as would the intermediates that would be required to implement the improved methods.

Neither 5-alkoxy-1,2,4-triazolo[4,3-c]pyrimidine-3(2H)-thione compounds nor 5-alkoxy[1,2,4]triazolo[1,5-c]pyrimidine-2(3H)-thione compounds have been described in the art. 3-Hydrocarbylthio-5-alkoxy-1,2,4-triazolo[4,3-c]pyrimidine compounds are also novel.

SUMMARY OF THE INVENTION

5-Alkoxy-1,2,4-triazolo[4,3-c]pyrimidine-3(2H)-thione compounds have now been prepared and found to be useful in the preparation of 5-alkoxy[1,2,4]triazolo[1,5-c]pyrimidine-2(3H)-thione compounds by rearrangement and, as a result, can be used as intermediates in the preparation of N-(substituted phenyl)-5-alkoxy[1,2,4]triazolo[1,5-c]pyrimidine-2-sulfonamide herbicides. The resulting process allows for the preparation of N-(substituted phenyl)-5-alkoxy[ 1,2,4]triazolo[1,5-c]pyrimidine-2-sulfonamide herbicides in a more economical and more readily carried out manner than the previously described process.

The invention includes 5-alkoxy-1,2,4-triazolo[4,3-c]pyrimidine-3(2H)-thione compounds of Formula I:

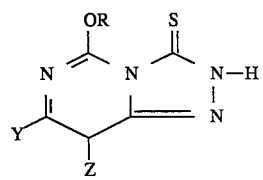

wherein one of Y and Z represents F, Cl, Br, R', or OR' and the other represents H; and R and R' each independently represents $CH_3$ or $C_2H_5$ and their trialkylammonium salts, which salts are adducts of said compounds and a trialkylamine compound having a pKa of about 9.4 to about 11.4.

Compounds of Formula I wherein one of Y and Z represents F, Cl, or Br and the other represents H are generally preferred. The fluorinated compounds are usually more preferred, but the chlorinated compounds are sometimes more preferred. Trialkylammonium salts wherein the trialkylamine involved is a compound of Formula II:

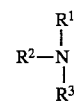

wherein $R^1$, $R^2$, and $R^3$ each independently represents $C_1$–$C_4$ alkyl or benzyl or two of $R^1$, $R^2$, and $R^3$ together represent a moiety of the formula —$(CH_2)_4$—, —$(CH_2)_5$—, $O(C_2H_4$—$)_2$, or $CH_3N(C_2H_4$—$)_2$ or all three of $R^1$, $R^2$, and $R^3$ together represent a moiety of the formula $N(C_2H_4$—$)_3$ are preferred salts; triethylammonium salts are specifically preferred.

The invention further includes a method of use of 5-alkoxy-1,2,4-triazolo[4,3-c]pyrimidine-3(2H)-thione compounds of Formula I:

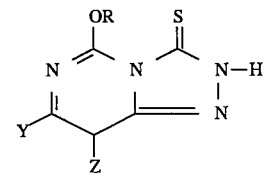

wherein one of Y and z represents F, Cl, Br, R', or OR' and the other represents H; and R and R' each independently represents $CH_3$ or $C_2H_5$ which method comprises treating said compound with at least about one molar equivalent of an alkali metal alkoxide of the formula ROM wherein R represents $CH_3$ or $C_2H_5$ and M represents an alkali metal in a medium containing an alcohol of the formula ROM wherein R represents $CH_3$ or $C_2H_5$, the alkali metal alkoxide and the alcohol selected so that R is the same in the alkali metal alkoxide, the alcohol, and the 5-alkoxy-1,2,4-triazolo[4,3-c]pyrimidine-3(2H)-thione compound, at a temperature of about −10° C. to about 40° C., and thereafter acidifying the mixture to obtain a 5-alkoxy[1,2,4]triazolo[1,5-c]pyrimidine-2(3H)-thione compound of Formula III:

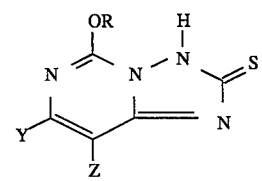

wherein R, Y, and Z are as defined before.

Compounds of Formula III wherein one of Y and Z represents F, Cl, or Br and the other represents H are preferred. Those wherein one of Y and Z represents F and the other represents H are usually more preferred and those wherein one of Y and Z represents Cl and the other represents H are sometimes more preferred.

The invention still further includes a method of use of trialkylammonium salts of 5-alkoxy-1,2,4-triazolo[ 4,3-c] pyrimidine-3(2H)-thione compounds, which salts are adducts of a compound of Formula I:

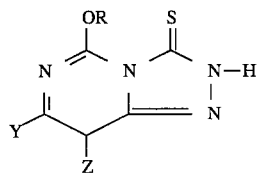

wherein
one of Y and Z represents F, Cl, Br, R', or OR' and the other represents H; and
R and R' each independently represents $CH_3$ or $C_2H_5$
and a trialkylamine compound having a pKa of about 9.4 to about 11.4, which method comprises treating said salt with at least about an equimolar amount of a benzyl halide or a $C_2$–$C_4$ alkyl halide in an inert solvent and obtaining a 3-hydrocarbylthio-5-alkoxy-1,2,4-triazolo[4,3-c]pyrimidine compound of Formula IV:

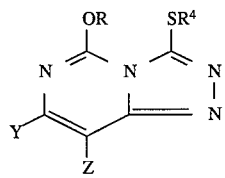

wherein X, Y, and R are defined as before and $R^4$ represents benzyl or $C_2$–$C_4$ alkyl.

Compounds of Formula IV wherein one of Y and Z represents F, Cl, or Br and the other represents H are usually preferred. Those wherein one of Y and Z represents F and the other represents H are usually more preferred and those wherein one of Y and z represents $C_1$ and the other represents H are sometimes more preferred. Compounds wherein $R^4$ represents benzyl are typically preferred.

3-Hydrocarbylthio-5-alkoxy-1,2,4-triazolo[4,3-c]pyrimidine compounds of Formula IV can be converted to corresponding 2-hydrocarbylthio-5-alkoxy[1,2,4]triazolo[1,5-c] pyrimidine compounds of Formula V:

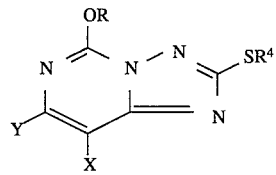

by treatment with an alkali metal alkoxide of the formula ROM wherein R represents $CH_3$ or $C_2H_5$ in a medium containing an alcohol of the formula ROH wherein R represents $CH_3$ or $C_2H_3$; the alkali metal alkoxide and the alcohol selected so that R is the same in the alkali metal alkoxide, the alcohol, and the 3-hydrocarbylthio-5-alkoxy-1,2,4-triazolo[4,3-c]pyrimidine compound.

DETAILED DESCRIPTION OF THE INVENTION

The compounds of the present invention can be characterized as 5-alkoxy-1,2,4-triazolo[4,3-c]pyrimidine- 3(2H)-thione compounds wherein the alkoxy group is methoxy or ethoxy and wherein there is a single halogen, alkyl, or alkoxy substituent in the 7- or 8-position and the reaction products of these compounds with trialkylamine compounds. They include 5-alkoxy- 1,2,4-triazolo[4,3-c]pyrimidine-3(2H)-thione compounds of Formula I:

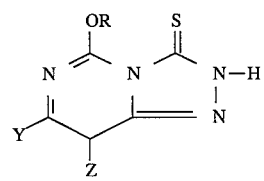

wherein R represents methyl or ethyl and one of Y and Z represents fluorine, chlorine, bromine, methyl, ethyl, methoxy, or ethoxy and the other represents hydrogen and their trialkylammonium salts. 5-Alkoxy-(7- or 8-fluoro, chloro, or bromo)-1,2,4-triazolo[4,3-c]pyrimidine-3(2H)-thione compounds are often preferred. The fluorinated compounds are typically more preferred but the chlorinated compounds are sometimes more preferred.

Some specifically preferred compounds of Formula I include 5-ethoxy-7-(fluoro or chloro)-1,2,4-triazolo [ 4,3-c] pyrimidine-3(2H)-thione, 5-methoxy-7-(fluoro or chloro)-1, 2,4-triazolo[4,3-c]-pyrimidine- 3 (2H)-thione, 5-ethoxy-8-(fluoro or chloro)-1,2,4-triazolo[ 4,3-c]pyrimidine-3(2H)-thione, and 5-methoxy-8-(fluoro or chloro)-1,2,4-triazolo[4, 3-c] pyrimidine-3(2H)-thione.

The compounds of Formula I are named and depicted herein as 3(2H)-thione compounds. They could equally well have been named and depicted as 3-thiol compounds since the two structures are keto-enol type isomers and are in dynamic equilibrium. The keto and enol isomers of the compounds of Formula I are shown below:

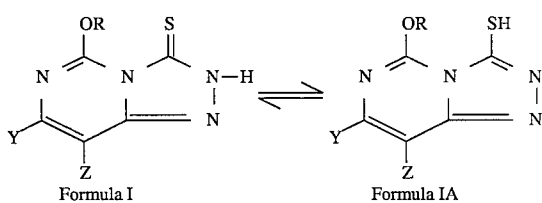

Formula I            Formula IA

The trialkylammonium salts of the compounds of Formula I can be looked upon as adducts of these compounds and a trialkylamine compound having a pKa of about 9.4 to about 11.4, such as a trialkylamine compound of Formula II:

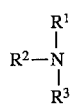

wherein $R^1$, $R^2$, and $R^3$ each independently represents alkyl of 1 to 4 carbon atoms or benzyl or two of $R^1$, $R^2$, and $R^3$ together, taken with the nitrogen atom, represent pyrrolidine, piperidine, morpholine, or N-methylpiperazine or all three of $R^1$, $R^2$, and $R^3$ together, taken with the nitrogen atom, represent 1,4-diazabicyclo[2,2,2]octane. The triethylammonium salts are preferred salts.

The 5-alkoxy-1,2,4-triazolo[4,3-c]pyrimidine-3(2H)-thione compounds of Formula I are not very stable and tend to decompose on standing, even in the solid state. It is preferred to utilize these compounds as intermediates in the synthesis of other, more stable compounds, soon after preparing them.

The 5-alkoxy-1,2,4-triazolo[4,3-c]pyrimidine-3(2H)-thione compounds of the present invention can be employed in a process for the preparation of 5-alkoxy[1,2,4]triazolo[1,5-c]pyrimidine-2(3H)-thione compounds of Formula III:

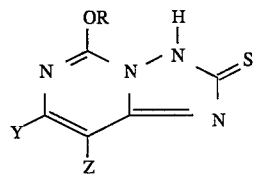

wherein R represents methyl or ethyl and one of Y and Z represents fluoro, chloro, bromo, methyl, ethyl, methoxy, or ethoxy and the other represents hydrogen. These compounds can be characterized as 1,2,4-triazolo[1,5-c]-pyrimidine-2(3H)-thione compounds having a methoxy or an ethoxy substituent in the 5-position and a halo, alkyl, or alkoxy substituent in the 7- or 8-position. The process involved in the method of use is preferably employed to prepare compounds of Formula III wherein one of Y and Z represents fluoro, chloro, or bromo and the other represents hydrogen. It is of special interest for the preparation of compounds of Formula III wherein one of Y and Z represents fluoro and the other represents hydrogen and is of considerable interest for compounds wherein one of Y and Z represents chloro and the other represents hydrogen.

Some specifically preferred compounds of Formula III that can be prepared include 8-fluoro- 5-methoxy[1,2,4]triazolo[1,5-c]pyrimidine-2(3H)-thione, 5-ethoxy-7-fluoro[1,2,4]triazolo[1,5-c]pyrimidine-2(3H)-thione, 8-chloro-5-methoxy[1,2,4,]triazolo[1,5-c]pyrimidine- 2(3H)-thione, and 7-chloro-5-ethoxy[1,2,4 ]triazolo[1,5-c]pyrimidine-2 (3H) -thione.

The compounds of Formula III are named and depicted herein as 2(3H)-thione compounds. They could equally well have been named and depicted as 2-thiol compounds since the two structures are keto-enol type isomers and are in dynamic equilibrium. The keto and enol isomers of the compounds of Formula III are shown below:

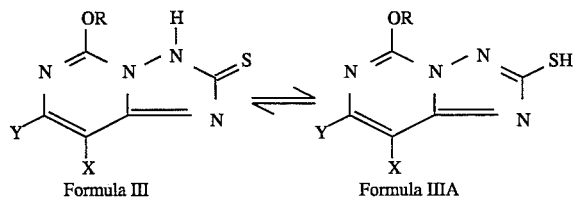

Formula III      Formula IIIA

The process by which compounds of Formula I are converted to compounds of Formula III involves combining a 5-alkoxy-1,2,4-triazolo[4,3-c]pyrimidine-3(2H)-thione compound of Formula I:

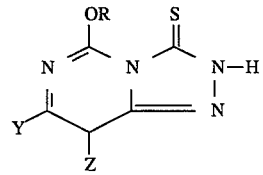

wherein R represents methyl or ethyl and one of Y and z represents fluoro, chloro, bromo, methyl, ethyl, methoxy, or ethoxy and the other represents hydrogen with at least about one molar equivalent of an alkali metal methoxide or ethoxide in an medium containing methanol or ethanol as the solvent or one of the solvents. The alkali metal alkoxide and the alcohol must be selected so that the 5-alkoxy group of the compound of Formula I, the alkoxide, and the alcohol all have the same alkyl group (methyl or ethyl). If the reagents are not so matched, exchange reactions take place which significantly reduce yields and complicate the recovery procedure.

The alkali metal alkoxides that are employed in the process are the lithium, sodium, and potassium derivatives of methanol and ethanol. At least about one molar equivalent of the alkali metal alkoxide is employed. Ratios of alkali metal alkoxide to the compound of Formula I of between about 1 and about 2 are typical. Ratios of about 1.03 to about 1.3 are generally preferred. Higher concentrations of alkali metal alkoxide are deleterious to the process.

The reaction medium of the process must contain the appropriate alcohol and may also contain other compatible solvents. Such solvents should be miscible with the alcohol involved, should not cause excessive precipitation of the alkali metal alkoxide, and should not be reactive with any of the reagents or products. Such compatible solvents include acetonitrile, 1,2-dimethoxyethane, N,N-dimethylformamide, dimethyl sulfoxide, and the like. It is preferred that the reaction medium contain less than about 2 percent water. It is more preferred that it contains less than 0.2 percent. The presence of water is responsible for side reactions that destroy the starting material, the product, or both. It is often preferred to use as little reaction medium as possible; complete solubility of the compounds of Formulas I and III in the medium is not required.

The isomerization proceeds well at ambient temperatures and is generally carried out at temperatures of about −10° C. to about 40° C. Temperatures of about 0° C. to about 30° C. are often preferred. The starting materials and products tend to decompose at higher temperatures. The fact that the process can be carried out at such low and convenient temperatures is an important feature of the process.

The process can be carried out in conventional vessels. The reaction mixture is typically agitated to ensure good mixing.

The rearrangement reaction takes place over the course of a few minutes to a few hours and a mixture containing an alkali metal salt of a compound of Formula III is initially obtained. It is preferred that this mixture not be allowed to stand for extensive periods of time because the salts of the desired compound of Formula III are not completely stable. The compounds of Formula III, themselves, are obtained by adding sufficient acid to neutralize the medium.

Essentially any organic or inorganic protic acid can be used for the acidification. Typically, a cheap and readily available acid having a pKa of less than 8, such as hydrochloric acid, sulfuric acid, or acetic acid is used. Hydrochloric acid is preferred. Typically, an amount of acid in excess of that required for exact neutralization is added.

The desired compound of Formula III can be recovered by collecting the precipitate that forms upon acidification. Water is typically added after acidification and before the collection to ensure complete precipitation. The recovered product can be collected by filtration or centrifugation and can be dried by conventional means, if desired, provided that excessive heat is avoided. These compounds can be further purified by conventional means, such as by recrystallization, liquid chromatography, and the like. They are not very stable, however, and tend to decompose on standing, even in the solid state. It is preferred to utilize these compounds as intermediates in the synthesis of other, more stable compounds soon after preparing them.

The compounds of Formula III can be converted to 2-hydrocarbylthio-5-alkoxy[1,2,4]triazolo[1,5-c]pyrimidine compounds of Formula V:

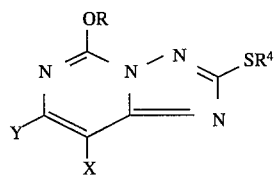

wherein R represents methyl or ethyl; one of X and Y represents fluoro, chloro, bromo, methyl, ethyl, methoxy, or ethoxy and the other represents hydrogen; and $R^4$ represents benzyl or $C_2$–$C_4$ alkyl. The conversion is effected by treating the compound of Formula III with a base, such as a triethylamine compound, sodium ethoxide, or potassium methoxide, and a benzyl halide or a $C_2$–$C_4$ alkyl halide, such as benzyl chloride or ethyl bromide, or a substantial equivalent thereof under mild reaction conditions. The reaction is typically carried out in methanol or ethanol solvent at ambient temperature or at a temperature up to about 50° C. with agitation to ensure mixing. Methanol and an alkali metal methoxide are preferably employed as the solvent and base, respectively, when the R of Formula III represents methyl and ethanol and an alkali metal alkoxide are, preferably, employed when R represents ethyl. Sodium alkoxides are preferred alkali metal alkoxides. The reaction conditions are essentially the same as those of similar alkylation reactions well-known in the art.

It is often convenient to convert the alkali metal salt of a compound of Formula III that is initially obtained in the method of use of compounds of Formula I process of the present invention into a compound of Formula V by adding a benzyl halide or a $C_2$–$C_4$ alkyl halide, such as benzyl chloride or ethyl bromide, or a substantial equivalent thereof to the reaction mixture rather than acidifying. The alkylation reaction can be carried out under the same reaction conditions already established in the reaction vessel or can be altered within the guidelines given above for optimum results. The compounds of Formula V obtained can be recovered by conventional means.

The trialkylammonium salts of 5-alkoxy-1,2,4-triazolo[4,3-c]pyrimidine-3(2H)-thione compounds that are adducts of a compound of Formula I:

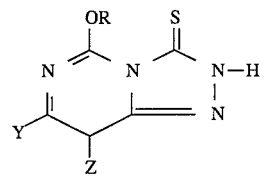

wherein R represents methyl or ethyl and one of Y and Z represents fluoro, chloro, bromo, methyl, ethyl, methoxy, or ethoxy and the other represents hydrogen and a trialkylamine compound having a pKa of about 9.4 to about 11.4 such as, but not limited to, a compound of Formula II:

wherein $R^1$, $R^2$, and $R^3$ each independently represents $C_1$–$C_4$ alkyl or benzyl or two of $R^1$, $R^2$, and $R^3$ together along with the nitrogen atom represent pyrrolidine, piperidine, morpholine, or N-methylpiperazine or all three of $R^1$, $R^2$, and $R^3$ together along with the nitrogen atom represent 1,4-diazabicyclo[2,2,2]octane can be employed for the preparation of a 3-hydrocarbylthio-5-alkoxy- 1,2,4-triazolo [4,3-c]pyrimidine derivative compounds of Formula IV:

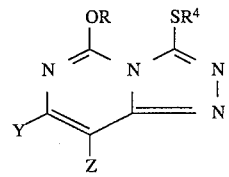

wherein X, Y, and R are defined as before and $R^4$ represents benzyl or $C_2$–$C_4$ alkyl. The use of trialkylammonium salts of compounds of Formula I wherein one of Y and Z represents fluoro, chloro or bromo and the other represents hydrogen are preferred. The use of such compounds wherein one of Y and z represents fluoro and the other represents hydrogen are usually more preferred and those wherein one of Y and z represents chloro and the other represents hydrogen are sometimes more preferred. The trialkylammonium salts derived from compounds of Formula II are usually preferred and triethylammonium salts ($R^1$, $R^2$, and $R^3$ each represent ethyl) are normally employed. The conversion of the salts to 3-benzylthio compounds ($R^4$ in Formula IV represents benzyl) is generally preferred.

The method is accomplished by combining a trialkylammonium salt of a compound of Formula I with a benzyl halide or a 2 to 4 carbon alkyl halide, such as benzyl chloride or ethyl bromide, or-a substantial equivalent thereof in a solvent in which the salt is at least partially soluble, such as acetonitrile/water, methanol, or ethanol, and allowing the mixture to stand at ambient temperature or heating it to about 40° C. to about 80° C. Excessive heating and large excesses of trialkylamine compound lead to undesirable side reactions. The reaction conditions are essentially the same as those known in the art for related alkylation reactions. The resulting compounds of Formula IV can be recovered by conventional means, such as by filtration or by evaporation of the solvents, and can be purified readily by conventional means, such as by liquid chromatography, recrystallization from a solvent, or extraction.

The trialkylammonium salt compounds employed in this method of use can be obtained by the reaction of a 2-alkoxy-4-hydrazinopyrimidine compound, carbon disulfide, and hydrogen peroxide in the presence of a trialkylamine compound as described hereinbelow. These compounds can also be obtained by the reaction of a compound of Formula I with a trialkylamine compound, such as a compound of Formula II. This preparation can be accomplished readily by dissolving a compound of Formula I in an organic solvent, such as acetonitrile, and adding at least about one mole of the trialkylamine compound. If a solvent in which the compound of Formula I is soluble but the trialkylammonium salt is insoluble is selected, the salt precipitates and can be recovered by filtration or centrifugation. The recovered salts can be dried by conventional means. If a solvent in which the salt is soluble, such as a 1:1 mixture of acetonitrile and water, is selected, the salt remains in solution and can be utilized in that form.

The 3-hydrocarbylthio-5-alkoxy-1,2,4-triazolo[4,3-c]pyrimidine compounds of Formula IV can be converted into 2-hydrocarbylthio-5-alkoxy[1,2,4]triazolo[1,5-c]pyrimidine compounds of Formula V:

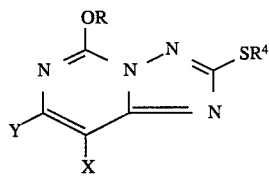

wherein R represents methyl or ethyl and one of Y and Z represents fluoro, chloro, bromo, methyl, ethyl, methoxy, or ethoxy and the other represents hydrogen by treatment with an alkali metal alkoxide under reaction conditions similar to those described hereinabove for the conversion of a compound of Formula I into a compound of Formula III except that less that an equimolar amount of the alkali metal alkoxide is required and the product is not a salt and does not require neutralization with an acid before recovery. Mole ratios of alkali metal alkoxide to compound of Formula IV of about 1:100 to about 1:1 are generally employed. Mole ratios of about 1:50 to about 1:4 are usually preferred. The isomerization is typically carried out in a medium containing an alcohol solvent. It is important that any alcohol in the medium, the alkali metal alkoxide, and the R of the compound of Formula IV all have the same alkyl group. Thus, when R represents methyl, an alkali metal methoxide and methanol are employed and when R represents ethyl an alkali metal ethoxide and ethanol are employed. Temperatures between about 0° C. and about 60° C. are typical; temperatures between about 10° C. and about 50° C. are usually preferred. The mixture is typically agitated during the reaction period to ensure good mixing. The compounds of Formula V can be recovered by conventional means, such as by adding water to ensure complete precipitation and subsequent filtration or centrifugation.

The compounds of Formula V are known from U.S. Pat. Nos. 5,163,995 and 5,177,206, the appropriate portions of which are hereby incorporated by reference, to be useful for the preparation of herbicidal 5-alkoxy[1,2,4]triazolo[1,5-c] pyrimidine-2-sulfonamide compounds. The compounds of Formula V can be converted to the corresponding 2-chlorosulfonyl compounds by treatment with chlorine in an aqueous medium and the 2-chlorosulfonyl compounds can be coupled with an appropriately substituted aniline or N-trialkylsilylaniline compound in an inert solvent, such as acetonitrile, in the presence of a tertiary amine and/or a catalytic amount of dimethyl sulfoxide. The compounds of Formula III can be converted directly into herbicidal 5-alkoxy[1,2,4]triazolo[1,5-c]pyrimidine- 2-sulfonamide compounds in a similar manner.

Alternately, and usually preferably, the compounds of Formula III can be converted into herbicidal 5-alkoxy[1,2, 4]triazolo[1,5-c]pyrimidine-2-sulfonamide compounds by oxidation with hydrogen peroxide to obtain a 2,2'-dithiobis(5-alkoxy[1,2,4]triazolo[1,5-c]pyrimidine) intermediate compound of Formula VI:

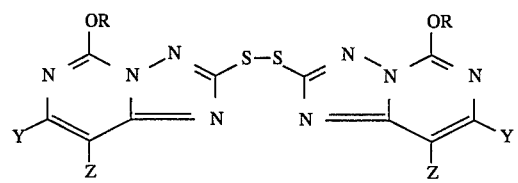

wherein R, Y, and Z are as defined before. These intermediates can be subsequently chloroxidized with chlorine in an aqueous medium to obtain the 2-chlorosulfonyl intermediates noted above. The oxidation is generally carried out by adding slightly in excess of 0.5 mole (1 equivalent) of hydrogen peroxide to the compound of Formula III in an aqueous solvent, such as aqueous acetonitrile, at ambient temperatures. The compound of Formula VI, which typically precipitates from the medium, can be recovered. It can be converted to a 2-chlorosulfonyl intermediate by treatment with chlorine in an aqueous medium, such as aqueous methylene chloride, at ambient temperatures or below. The 2-chlorosulfonyl intermediates can be converted to the desired herbicides by the methods described in the prior art cited above.

The 5-alkoxy-1,2,4-triazolo[4,3-c]pyrimidine-3(2H)-thione compounds of Formula I can be prepared by combining a 2-alkoxy-4-hydrazinopyrimidine compound of Formula VII:

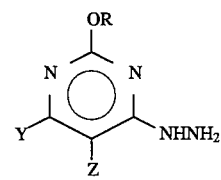

wherein R represents methyl or ethyl and one of Y and Z represents fluoro, chloro, bromo, methyl, ethyl, methoxy, or ethoxy and the other represents hydrogen with at least about one mole of carbon disulfide and, optionally, a trialkylamine compound having a pKa of about 9.4 to about 11.4, such as a compound of Formula II:

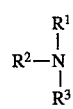

wherein $R^1$, $R^2$, and $R^3$ each independently represents $C_1$–$C_4$ alkyl or benzyl or two of $R^1$, $R^2$, and $R^3$ together represent a moiety of the formula —(CH$_2$)$_4$—, —(CH$_2$)$_5$—, O(C$_2$H$_4$—)$_2$, or CH$_3$N(C$_2$H$_4$—)$_2$ or all three of R$^1$, R$^2$, and R$^3$ together represent a moiety of the formula N(C$_2$H$_4$—)$_3$. The reagents are combined in a suitable inert liquid medium, such as aqueous acetonitrile, and at least about one mole of an oxidizing agent, such as hydrogen peroxide, is added at a temperature of about 0° C. to about 40° C. The mixture is typically agitated to assure good mixing. The reaction proceeds quickly with the formation the desired 5-alkoxy-1,2,4-triazolo[4,3-c]pyrimidine-3(2H)-thione compound of Formula I or, if a trialkylamine compound is added, a trialkylammonium salt thereof. If a trialkylammonium salt is obtained, it can be converted into a compound of Formula I by adding at least one mole of a strong acid, such as hydrochloric acid. The compounds of Formula I obtained can be recovered by adding water to ensure complete precipitation and collecting the precipitate by filtration or centrifugation. The by-product elemental sulfur can be removed by conventional means. The differences in solubility between sulfur and the compounds of Formula I in aqueous bases (compound of Formula I soluble and sulfur insoluble) and in carbon disulfide (the opposite) are typically exploited.

The 2-alkoxy-5-substituted-4-hydrazinopyrimidine starting materials of Formula VII can be prepared from 2,4-dialkoxy-5-substituted-pyrimidine compounds by treatment with hydrazine and triethylamine. Similarly, the 2-alkoxy-6-substituted-4-hydrazinopyrimidine compounds can be prepared from the corresponding 2-alkoxy-4-halo-6-substituted-pyrimidine compounds by treatment with hydrazine and triethylamine. The reactions are best carried out in water or in a solvent, such as acetonitrile, at a temperature of between about 0° C. about 40° C., using about one mole of triethylamine and slightly in excess of one mole of hydrazine hydrate. The desired 2-alkoxy-(5 or 6)-substituted-4-hydrazinopyrimidine compounds of Formula VII can be recovered by adding water to promote precipitation and recovering the precipitate by filtration, centrifugation, or extraction. These compounds can, however, often be employed as intermediates without recovery and/or purification.

The following examples are presented to illustrate the invention. They should not be construed as limitations on the claims.

EXAMPLES

1. Preparation of
5-Fluoro-4-hydrazino-2-methoxyprimidine

5-Fluoro-2,4-dimethoxypyridine (158 g (grams), 1.00 mol), 150 g (3.00 mol) of hydrazine hydrate, and 237 g of methanol were placed in a 1 L (liter) flask and heated to reflux (about 70° C.) for 3.5 hours with stirring. The mixture, which became homogeneous and then heterogeneous again, was then cooled to 0°–5° C. and the solids present were recovered by vacuum filtration, washed with 150 mL (milliliters) of cold methanol, and dried to constant weight. The title compound, which was obtained as colorless needles melting at 188°–189° C., amounted to 151.5 g (98 percent of theory).

NMR data (DMSO-d6) δ: $^1$H: 3.77 (s, 3H), 4.38 (2H), 7.83 (d(J=3.6 Hz), 1H), 8.87 (1H); $^{13}$C: 54.2,137.9 (d(J$_{CF}$= 19.6 Hz )), 141.5 (d(J$_{CF}$=244.8 Hz )), 154.3 (d(J$_{CF}$=13.7 Hz )), 160.6.

2. Preparation of
2ethoxy-4-fluoro-6-hydrazinopyrimidine

A mixture of 100 g of 94 percent purity (0.59 mol) 2-ethoxy-4,6-difluoropyrimidine, 275 mL of acetonitrile, and 107 g of water was prepared and cooled to 10° C. To this was added 68 g (0.67 mol) of triethylamine and then 34 g (0.68 mol) of hydrazine hydrate, slowly with stirring and cooling (at 5° to 10° C.). When all of the hydrazine had been added, the mixture was stirred another 15 min with cooling and was then allowed to warm. After a total of 1 hour, the solids that formed were recovered by vacuum filtration and were washed twice with 100 mL portions of water and then with 50 mL of ethanol. The title compound, which was obtained as a white solid melting at 141°–143° C., amounted to 79.7 g (80 percent of theory).

Elemental Analysis for C$_6$H$_9$FN$_4$O: Calc.: %C, 41.9; %H, 5.27; %N, 32.5 Found: %C, 42.2; %H, 5.12; %N, 32.6

3. Preparation of
5-Chloro-4.-hydrazino-2-methoxypyrimidine

A solution containing 0.35 g (2.0 mmol) of 5-chloro-2,4-dimethoxypyrimidine and 0.35 g (7.0 mmol) of hydrazine hydrate in 2.9 g of methanol was heated at reflux with stirring for 8 hours. The mixture was then cooled causing a precipitate to form. Water was added until the precipitation appeared to be complete and the precipitate was then recovered by vacuum filtration and allowed to air dry overnight to obtain 0.23 g (66 percent of theory) of the title compound as a white solid. The product melted at 172°–173° C. after changing crystalline form from needles to cube-like shapes in a phenomenon that appeared to involve sublimation.

NMR data (DMSO-d6) δ: $^1$H: 3.85 (s, 3H), 4.50 (2H), 7.97 (s, 1H), 8.7 (1H); $^{13}$C: 54.17, 105.40, 152.77, 159.39, and 163.39.

4. Preparation of
8-Fluoro-5-methoxy-1,2,4-triazolo[4,3-c]pyrimidine-3(2H)-thione 5-Fluoro-4-hydrazino-2-methoxypyrimidine (15.81 g, 0.100 mol), 47 g of methanol, 10.2 g (0,100 mol) of triethylamine, and 11.4 g (0.15 mol) of carbon disulfide were combined in a 250 mL flask under nitrogen at ambient temperature with stirring to obtain a yellow, heterogeneous mixture. The mixture was cooled to 15° C. with an ice bath. Hydrogen peroxide (12.5 g of 30 percent aqueous, 0.11 mol) was then added by means of a syringe pump, the syringe of which was inserted into the flask through a septum. The addition was made over a 1-hour period with stirring and cooling to maintain the temperature at about 15° C. The mixture was allowed to react and warm for 1 hour and the resulting heterogeneous orange mixture was vacuum filtered to remove the solid sulfur. The filtrate was cooled in an ice bath and acidified with 17.6 mL (0.11 mol) of 6.25N hydrochloric acid diluted with 125 mL of water. The resulting precipitate was recovered by vacuum filtration and dried under reduced pressure to obtain 18.81 g (94 percent of theory) of the title compound as an off-white solid melting at 166° C. with decomposition.

NMR data (DMSO-d6) δ: $^1$H: 4.01 (s, 3H), 7.64 (d(J=2.8 Hz), 1H), 14.5 (brs, 1H); $^{13}$C: 56.00, 125.6 (d(J$_{CF}$=22.0 Hz)), 141.6, 141.7 (d(J$_{CF}$=41.7 Hz)), 146.0 (d(J$_{CF}$=191.0 Hz)), and 161.2.

5. Preparation Of 5-Ethoxy-7-fluoro-2,4-triazolo[4,3-c]pyrimidine-3(2H)-thione Procedure A: A mixture containing approximately 5.2 g (30 mmol) of 2-ethoxy-4-fluoro-6-hydrazinopyrimidine in a solvent composed of 50 mL of acetonitrile and 15 mL of water was prepared and to this was added 6.4 mL (107 mmol) of carbon disulfide at ambient temperature with stirring. The heterogeneous white mixture became a pale yellow solution after about 10 min and then 3.8 mL of 30 percent aqueous hydrogen peroxide (37 mmol) and 3.2 mL of water were added over a 30-min period with stirring and cooling to hold the temperature at about 25° C. The mixture was allowed to react another 10 min and then 3.22 g (32 mmol) of triethylamine was added and the resulting mixture was filtered to remove sulfur. The filtrate was acidified with 10 mL of 3.75N hydrochloric acid (38 mmol) and the resulting mixture was filtered to recover the precipitate that formed. This was washed with water and dried to obtain 4.4 g (66 percent of theory) of the title compound of 97 percent purity as a light beige solid melting at 170° C. Considerable product remained in the filtrate.

Elemental Analysis for $C_7H_7FN_4OS$: Calc.: %C, 39.2; %H, 3.29; %N, 26.2 Found: %C, 39.3; %H, 3.07; %N, 25.9

Procedure B: A mixture containing 32.6 g (0,186 mol) of 2-ethoxy-4-fluoro-6-hydrazinopyrimidine and 21.1 g (0.277 mol) of carbon disulfide in a solvent composed of 83.7 mL of acetonitrile and 33.3 mL of water was prepared under nitrogen in a 500 mL flask equipped with a condensor and an opening covered by a septum through which the syringe of a syringe pump was inserted. The mixture was allowed to react with stirring at ambient temperature for 15 min and then 22.2 g of 30 percent aqueous hydrogen peroxide (0.196 mol) was added over a 1-hour period by means of the syringe with stirring and cooling to hold the temperature at about 25° C. The mixture was allowed to react for another hour and then was cooled to about 0° C. The precipitated product and sulfur by-product were recovered by vacuum filtration and washed with 150 mL of water, 150 mL of a 1:1 mixture of water and acetonitrile, and finally with two 75 mL portions of acetonitrile and were then air dried to obtain 45.1 g of a light beige product that was 74.8 percent the title compound (85 percent of theory yield), 13.9 percent sulfur, and 0.5 percent water.

6. Preparation of 5-Ethoxy-7-fluoro-1,2,4-triazolo[4,3-c]pyrimidine-3(2H)-thione From 2-ethoxy-4,6-difluoropyrimidine A mixture consisting of 1.42 parts of acetonitrile, 2.66 parts of water, 1.60 parts of 2-ethoxy-4,6-difluoropyrimidine, and 1.06 parts of triethylamine is prepared and cooled to 5° C. Hydrazine hydrate (0.526 parts is added with cooling and stirring under nitrogen at a rate such that the temperature does not rise above 10° C. When the addition is complete, the mixture is allowed to warm to ambient temperature and stir until the reaction is complete. Carbon disulfide (1.14 parts) is then added with stirring and the mixture is allowed to react for 15 min. Hydrogen peroxide as a 30 percent solution in water (1.20 parts) is then added with stirring and cooling to maintain the temperature between 25° and 30° C. and the mixture is allowed to react for an additional hour at 25° C. The mixture is cooled to 0° C. and filtered in a reduced pressure apparatus to recover the insoluble material. This material is washed sequentially with 3.20 parts of water and 4.00 parts of cold acetonitrile to obtain the title compound mixed with by-product sulfur and containing up to 2 percent water and some acetonitrile.

7. Preparation of 7-Chloro-5-ethoxy-1,2,4-triazolo[4,3-C]pyrimidine-3(2H)-thione A mixture containing 20 g of 93 percent purity (99 mmol) 4-chloro-2-ethoxy-6-hydrazinopyrimidine in a solvent composed of 90 mL of acetonitrile and 26 mL of water was prepared under nitrogen in a 500 mL flask equipped with a condensor and an opening covered by a septum through which the syringe of a syringe pump was inserted. To this was added 11.3 g (148 mmol) of carbon disulfide and, after a 15-min reaction period, 16.7 g of 30 percent aqueous hydrogen peroxide (147 mmol) was added over a 15-min period by means of the syringe with stirring and cooling to hold the temperature at about 25° C. The mixture was allowed to react for another 4 hours and then was cooled to about 0° C. The precipitated product and sulfur by-product were recovered by vacuum filtration and washed with water, a 1:1 mixture of water and acetonitrile, and finally acetonitrile. The wet cake was slurried in 1 L of water at 70° C. and about 600 mL of acetonitrile was added to dissolve the solid. The resulting mixture was gravity filtered and the filtrate was allowed to cool over the weekend. The mixture was further cooled in a refrigerator and the crystals that formed were recovered by vacuum filtration, washed with acetonitrile, and dried to constant weight to obtain 14.1 g (62 percent of theory) of the title compound as an amber solid which decomposed on heating above 187° C.

Elemental Analysis for $C_7H_7ClN_4OS$: Calc.: %C, 36.4; %H, 3.06; %N, 24.3 Found: %C, 36.4; %H, 2.79; %N, 24.1

8. Preparation of 8-Chloro-5-methoxy-1,2,4-triazolo[4,3-c]pyrimidine-3(2H)-thione 5-Chloro-4-hydrazino-2-methoxypyrimidine (17.45 g, 0.10 mol) and 25 g (0.033 mol) of carbon disulfide were combined in 120 mL of acetonitrile and 30 mL of water at ambient temperature with stirring and 11.4 g (0.10 mol) of 30 percent hydrogen peroxide was added to the resulting mixture with stirring over a 2-hour period. The temperature rose from 20° C. to 48° C. Analysis of the mixture by high pressure liquid chromatography (HPLC) indicated that the reaction was complete. A 79.8 g (47.2 percent of the total) portion of the reaction mixture was diluted with 50 mL of water and the mixture was acidified with hydrochloric acid. The solids present were then recovered by vacuum filtration and dried to obtain 10.15 g of a mixture of the title compound and sulfur. The sulfur was then removed by extracting the solids with 45 g of carbon disulfide to obtain 8.08 g (80 percent of theory) of the title compound as a tan powder. This material was 92 percent pure by HPLC analysis; it decomposed on heating.

NMR data (DMSO-d6) $\delta$: $^1H$: 4.04 (s, 3H), 7.67 (s, 1H), 14.25 (brs, 1H); $^{13}C$: 56.18, 110.08, 140.46, 145.76, 150.11, and 161.32.

9. Preparation of 3-Benzylthio-8-fluoro-5-methoxy-1,2,4-triazolo[4,3-c]pyrimidine and 2-Benzylthio-8-fluoro-5-methoxyl[1,2,4]triazolo[1,5-c]pyrimidine 5-Fluoro-4-hydrazino-2-methoxypyrimidine (29.7 g, 0.188 mol), 100 g of methanol, 19.2 g (0.188 mol) of triethylamine, and 28.9 g (0.38 mol) of carbon disulfide were combined in a 500 mL flask under nitrogen at ambient temperature. Hydrogen peroxide (27 g of 30 percent aqueous, 0.24 mol) was then added by means of a syringe pump, the syringe of which was inserted into the flask through a septum, with cooling to maintain the temperature at 17° to 22° C. and with stirring. The addition was made over a 1.6-hour period. The mixture was allowed to react for another 1.5 hour and the resulting heterogeneous orange mixture was vacuum filtered to remove the solid sulfur. The solids were washed with 100 g of methanol and the filtrate (including the wash methanol), which contained the triethylammonium salt of 8-fluoro-5-methoxy-1,2,4-triazolo[4,3-c]-pyrimidine-3 (2H)-thione, was transferred to a reaction flask. Benzyl chloride (24.1 g, 0.19 mol) was added at 21° C. with stirring. There was a mild exotherm which increased the temperature to 27° C. and, after about 30 min, a precipitate began to form. After 1 hour, 130 g of methanol was removed by distillation under about 600 Pascals pressure and the heterogeneous residue was subsequently cooled to about 5° C. and vacuum filtered to recover the insoluble solids. About 25 g of methanol was used to aid in the transfer of the mixture and to wash the precipitate. The wet cake obtained amounted to 55.8 g and contained approximately 42 g (0.14 mol, approximately 95 percent of theory) of 3-benzylthio-8-fluoro-5-methoxy- 1,2,4-triazolo[4,3-c]pyrimidine-3(2H)-thione.

NMR data (CDCl$_3$) δ: $^1$H: 4.11 (s, 3H), 4.61 (s, 2H), 7.3 (m, 4H), and 7.4 (m, 2H); $^{13}$C: 36.7, 56.5, 123.3,123.6, 127.8, 128.6, 129.3, 135.9, 142.3, 144.2, 144.5, 145.7, 145.8, and 146.2.

The wet cake from above was diluted with 125 g of methanol and 2.9 g (0.013 mol) of 25 percent by weight sodium methoxide in methanol was added with stirring at ambient temperature in several portions. The mixture thickened. After 1.5 hour a solution of 2.4 mL (.0.15 mol) of 6.25N aqueous hydrochloric acid in 125 mL of water was added with stirring and cooling by means of an ice bath. The mixture was cooled to about 5° C., diluted with 80 g of water, vacuum filtered to recover the insoluble solids, and dried under reduced pressure to obtain 40.3 g (95 percent of theory) of the title compound as a colorless solid. This compound was identical spectroscopically and by quantitative HPLC with the compound reported in U.S. Pat. No. 5,163,995.

NMR data (DMSO-d6) δ: $^1$H: 4.17 (s, 3H), 4.51 (s, 2H), 7.3 (m, 3H), 7.45 (d(J=7.2 Hz), 2H), and 8.13 d(J=4.0 Hz), 1H; $^{13}$C: 34.8, 56.4, 127.3,128.4, 128.6, 128.8, 136.7, 141.4, 144.7, 145.4, 147.1, 147.5, and 161.6.

10. Preparation of 8-Fluoro-5-methoxy[1,2,4]triazolo[1,5-c]pyrimidine-2(3H)-thione.

A mixture of 10.01 g (0.050 mol) of 8-fluoro- 5-methoxy-1,2,4-triazolo[4,3-c]pyrimidine-3(2H)-thione in 8.6 g of methanol was prepared and cooled with an ice water bath. Sodium methoxide in methanol (32.4 g of 25 percent, 0.15 mol) was added under nitrogen with stirring and cooling. After 2.5 hours, 25.6 mL of ice cold 6.25N aqueous hydrochloric acid was added with stirring to the thick slurry obtained. The resulting mixture was diluted with a little water and the solids were recovered by vacuum filtration and dried under reduced pressure to obtain 8.26 g (83 percent of theory) of the title compound as a colorless powder. The compound melts at 155°–160° C. and then resolidifies and does not remelt up to 230° C.

NMR data (CD$_3$CN) δ: $^1$H: 2.5–3.5 (br s, 1H), 4.21 (s, 3H), 7.92 (d(J=2.1 Hz), 1H); $^{13}$C: 57.4, 118.2, 129.2, 129.5, 43.0, 146.4, 146.7, 148.7, 149.1, and 163.8.

11. Preparation of 5-ethoxy-7-fluoro[1,2,4]triazolo[1,5-c]pyrimidine-2(3H)-thione A mixture of 5.8 g (26 mmol) of 5-ethoxy- 7-fluoro-1,2,4-triazolo[4,3-c]pyrimidine-3(2H)-thione in 50 mL of absolute ethanol was prepared and to this was added at 0° C. with vigorous stirring and cooling 12.2 mL (33 mmol) of 21 weight percent sodium ethoxide in ethanol. A mildly exothermic reaction took place and the mixture changed from a suspension to a plum colored solution. The mixture was stirred at below 10° C. for 2.25 hours to complete the reaction. It was then acidified with 25 mL of 1.25N hydrochloric acid, stirred at −10° C. for 30 min, and filtered to recover the precipitate that formed. The precipitate was washed with 10 mL of cold water and dried to obtain 3.3 g (60 percent of theory) of the title compound of 98 percent purity. A second crop amounting to 1.7 g of 60 percent purity material (19 percent of theory) was obtained from the filtrate. The title compound melts at 83.5° C. to 86.5° C. and is a white solid.

NMR data (CDCl$_3$) δ: $^1$H: 1.58 (t, 3H), 4.52 (s, 2H), 4,75 (q, 2H), 7.28 (m, 3H), 7.45 (d, 2H).

The identity of the compound was further demonstrated by converting it into 2-benzylthio-5-ethoxy-7-fluoro[1,2,4]triazolo[1,5-c]pyrimidine, melting at 78°–82° C., by treatment with benzyl chloride.

12. Preparation of 8-Chloro-5-methoxy[1,2,4]triazolo[1,5-c]pyrimidine-2(3H)-thione 8-Chloro-5-methoxy-1,2,4-triazolo[4,3-c]-pyrimidine-3(2H)-thione (0.215 g, 1.00 mmol) was mixed with 2.0 g of dry methanol and to this mixture was added, in increments with stirring at ambient temperature, 0.26 g (1.2 mmol) of commercial 25 percent sodium methoxide in methanol. After a 35-min reaction period, the mixture was acidified with aqueous hydrochloric acid and diluted with water. The precipitate that formed was recovered by filtration and dried to obtain 0.168 g of the title compound in 97 percent purity as determined by HPLC (76 percent of theory) as a cream colored solid. The compound can be recrystallized from a mixture of methanol and water; it decomposes, but does not melt up to 250° C.

NMR data (CDCl$_3$) δ: $^1$H: 4.28 (s, 3H), 7.93 (s, 1H) over 14 (not observed); $^{13}$C: 56.0, 112.0, 142.1, 148.0, 153.5, and 163.0.

The identity of the product was further demonstrated by converting it into 2-benzylthio-8-chloro-5-methoxy[1,2,4]triazolo[1,5-c]pyrimidine, a compound known in U.S. Pat. No. 5,163,995, by treatment with benzyl chloride.

13. Preparation of 3-Benzylthio-5-ethoxy-7-fluoro-1,2,4-triazolo[4,3-c]pyrimidine from 2-Ethoxy-4-fluoro-6--hydrazinopyrimidine A 1.74 g (10 mmol) sample of 2-ethoxy-4-fluoro- 6-hydrazinopyrimidine was dissolved in 20 mL of absolute ethanol and 2.84 g (37 mmol) of carbon disulfide and 3.20 g (10 mmol) of 21 percent by weight sodium ethoxide were added. The mixture was heated at reflux with stirring for 3 hours and then was cooled by adding 20 mL of ice water. The mixture was then acidified to a pH of about 2 by adding 2 mL of 6.25N hydrochloric acid diluted to 8 mL with water. The yellow precipitate that formed was recovered by filtration, washed with water, and dried to obtain 0.85 g (40 percent of theory) of 5-ethoxy-7-fluoro-1,2,4-triazolo[4,3-c]pyrimidine-3(2H)-thione. The proton and carbon NMR spectra of this material were consistent with its assigned structure.

A 0.22 g portion of the product obtained above was dissoved in 2.5 g of absolute ethanol and 0.18 g of benzyl chloride and then 0,114 g of triethylamine were added with stirring at ambient temperature. When the starting material disappeared as determined by HPLC, the reaction mixture was added slowly to an excess of dilute aqueous hydrochloric acid. The beige crystals that formed were recovered by filtration, washed with water, and dried to obtain 0.27 g of 3-benzylthio-5-ethoxy-7-fluoro- 1,2,4-triazolo[4,3-c]pyrimidine as a solid. The proton and carbon NMR spectra of this material were consistent with its assigned structure.

14. Preparation of 2-Benzylthio-5-ethoxy-7-fluoro[1,2,4]triazolo[1,5-c]pyrimidine by Isomerization of 3-benzylthio-5-ethoxy-7-fluoro-1,2,4-triazolo[4,3-c]pyrimidine A solution of sodium ethoxide in ethanol was obtained by dissolving one drop (15 mg, 0.05 mmol) of 21 percent by weight sodium ethoxide in enough ethanol to make 0.17 g total. Ten drops of this were then added to 0.15 g of 3-benzylthio-5-ethoxy-7-fluoro-1,2,4-triazolo[ 4,3-c]pyrimidine in 4 g of absolute ethanol. The cloudy mixture became clear and after 1 hour sufficient water was added to cause the product to precipitate. The precipitate was recovered by filtration, washed with water, and dried to obtain 0.14 g (93 percent of theory) of the title compound as a white solid melting at 83.5°–84° C.

15. Preparation of 2,2'-Dithiobis(8-fluoro-5-methoxy[1,2,4]triazolo[1,5-c ]pyrimidine)

A heterogeneous mixture composed of 76.0 g (0.380 mol) of 8-fluoro-5-methoxy[1,2,4]triazolo[1,5-c ]pyrimidine-2(3H)-thione and 400 g of methanol at 24° C. was prepared and 45.3 g (0.400 mol) of ice cold 30 percent by weight hydrogen peroxide solution was added with stirring. An exothermic reaction took place raising the temperature to 43° C. The mixture was allowed to react for about 75 min and then another 13.0 g (0,115 mol) of ice cold 30 percent by weight hydrogen peroxide solution was added with stirring. The mixture was allowed to react for another 30 m in and then the solids present were recovered by vacuum filtration. These solids were dried and were then slurried with methanol. The slurry was heated to reflux, cooled to 35°– 45° C., and filtered to recover the insoluble solids. The solids were dried under reduced pressure at 40° C. to obtain 61.9 g of the title compound (80 percent of theory) as an off-white solid. The compound is a white powder melting at 201°–208° C. (dec.).

NMR data (DMSO-d6) δ: $^1$H: 4.16 (s, 3H), 8.21 (d(J=2.1 Hz), 1H).

16. Preparation of 2,2'-Dithiobis(5-ethoxy-7-fluoro[1,2,4]triazolo[1,5-c]pyrimidine)

A solution of 2.9 g (13.5 mmol) of 5-ethoxy-7-fluoro[1,2,4]triazolo[1,5-c]pyrimidine-2(3H) -thione in 30 mL of acetonitrile was prepared and 0.80 mL (7.8 mmol) of 30 percent hydrogen peroxide was added at ambient temperature with stirring under nitrogen. The temperature rose from 21° to 34° C. The mixture was allowed to react for about 1 hour and then 15 mL of water was added and the mixture was cooled to −5° C. The precipitate that formed was recovered by vacuum filtration, washed with two 10 mL portions of a 1:1 mixture of water and acetonitrile at 5° C., and dried to obtain 2.7 g (93 percent of theory) of the title compound as a light beige powder melting at 215°–216° C.

Elemental Analysis for $C_{14}H_{12}F_2N_8O_2S_2$: Calc.: %C, 39.4; %H, 2.83; %N, 26.3 Found: %C, 39.6; %H, 2.75; %N, 25.9.

17. Preparation of 2,2'-Dithiobis(5-ethoxy-7-fluoro[1,2,4]triazolo[1,5-c]pyrimidine) From 5-Ethoxy-7-fluoro-1,2,4-triazolo[4,3-c]pyrimidine-3(2H-thione Procedure A: A mixture of 167 g (0.76 mol) of 5-ethoxy-7-fluoro[1,2,4]triazolo[4,3-c]pyrimidine-3(2H)-thione and 1.67 L of toluene denatured absolute ethanol was prepared and to this was added 331 mL (0.887 mol) of 21 percent sodium ethoxide in ethanol at 0° C. with vigorous stirring and cooling. The reaction proceeded with a small exotherm and the heterogeneous light beige mixture became a plum colored solution. This solution was maintained at a temperature of between 5° C. and 10° C. for 2.25 hours and was then acidified with 150 mL of 6.25N hydrochloric acid diluted with 685 mL of water. The resulting mixture was allowed to warm to ambient temperature (23° C.) and then 43.4 mL of 30 percent aqueous hydrogen peroxide (0.43 mole) was added with stirring. The temperature rose to 33° C. and after 30 min all of the thione starting material was consumed as determined by HPLC. The mixture was cooled to 20° C. and the title compound, which precipitated, was recovered by filtration and washed at 5° C. with two 600 mL portions of water and then 350 mL of 50 percent aqueous ethanol. The white solid obtained was dried under reduced pressure at 35° C. to obtain 154 g of the title compound of about 90 percent purity as estimated by HPLC (86 percent of theory). Procedure B: A solid mixture that is 68 percent pure by analysis and contains 1.89 parts of 5-ethoxy-7-fluoro- 1,2,4-triazolo[4,3-c]pyrimidine-3(2H)-thione along with sulfur, less than 2 percent water, and some acetonitrile is diluted with 8.61 parts of absolute ethanol and the mixture is cooled to 10° C. A 21 percent sodium ethoxide by weight in ethanol solution (3.21 parts) is added with stirring and, after a few minutes, the mixture is filtered to remove the sulfur, retaining the filtrate. The sulfur is washed with 0.484 parts of absolute ethanol and the filtered wash ethanol is added to the filtrate. The filtrate mixture is allowed to react at 10° C. until isomerization is complete. The mixture is then acidified with 1.16 parts of 37 percent aqueous hydrochloric acid with stirring and cooling to keep the temperature below 25° C. A 30 percent by weight solution of hydrogen peroxide in water (0.602 parts) is added slowly with stirring and cooling to keep the temperature below 30° C. and the mixture is stirred an additional 30 min after the addition is complete. The precipitate that forms is recovered by filtration in a reduced pressure apparatus and is washed with 3.40 parts of ethanol and 8.70 parts of water to obtain the title compound as a water-wet solid.

18. Preparation of 2,2'-Dithiobis(5-ethoxy-7-fluoro[1,2,4]triazolo[1,5-c]pyrimidine) From 4,6-Difluoro-2-ethoxypyrimidine A mixture consisting of 32.7 g (0.202 mol) of 2-ethoxy-4,6-difluoroethoxypyrimidine, 59 g of acetonitrile, and 36 g of water was prepared in a reaction vessel and the mixture was stirred under nitrogen and cooled to about 5° C. To this was added 21.3 g (0.208 mol) of triethylamine and then 10.6 g (0.208 mol) of hydrazine monohydrate with stirring and cooling at a rate that maintained the reaction temperature at less than 15° C. After all of the hydrazine monohydrate had been added and the exotherm had subsided, the mixture was allowed to warm to ambient temperature to complete the reaction. A solution containing about 32.7 g (0.202 mol) of 2-ethoxy-4-fluoro-6-hydrazinopyrimidine in approximately 95 g of aqueous acetonitrile was obtained.

The solution of 2-ethoxy-4-fluoro-6-hydrazinopyrimidine in aqueous acetonitrile obtained above was placed into a reaction vessel and 23.1 g (0.303 mol) of carbon disulfide was added with stirring under nitrogen. After about 15 min, 23.8 g (0.210 mol) of 30 percent by weight aqueous hydrogen peroxide was added with stirring and cooling to hold the temperature at about 25°–30° C. A precipitate formed. The mixture was allowed to react for about 1 hour and was then cooled to 0° C. It was then filtered to recover the precipitate. The precipitate was washed first with two 75 mL portions of cold water to remove impurities and then with two 50 mL portions of cold acetonitrile to remove water. The 48.7 g of solid material obtained was determined to be 71 percent 5-ethoxy-7-fluoro-1,2,4-triazolo[4,3-c]pyrimidine-3(2H)-thione by HPLC (35 g, 80 percent of theory) and to contain less than 2 percent water by Karl Fischer titration. Elemental sulfur by-product was the major contaminant.

The 48.7 g (0.16 mol) of 5-ethoxy-7-fluoro- 1,2,4-triazolo [4,3-c]pyrimidine-3(2H)-thione as a 71 percent mixture with sulfur and acetonitrile obtained above was combined with 150 g of dry ethanol and the mixture was cooled to about 0° C. To this was added 67.7 g (0.21 mol) of 21 percent sodium ethoxide in ethanol with cooling and stirring such that the temperature was maintained between 5° and 15° C. The pH of the mixture was about 12. The mixture was filtered to remove the solid, insoluble sulfur and it was washed with 20 g of dry ethanol. The filtrate (including the wash ethanol) was allowed to react at about 7° C. for about another 2 hours and then 21.7 g (0.22 mol) of concentrated hydrochloric acid was added to obtain 5-ethoxy-7-fluoro[1,2,4]triazolo[ 1,5-c]pyrimidine-2(3H)-thione as a thin slurry of a light beige solid in ethanol.

The mixture of 5-ethoxy-7-fluoro[1,2,4]triazolo[ 1,5-c] pyrimidine-2(3H)-thione in ethanol obtained above was treated with 22.6 g (0.199 mol) of 30 percent hydrogen peroxide with stirring at ambient temperature. There was a mild exotherm. After a 40 min reaction period, the resulting mixture was filtered to recover the precipitate. This was washed with two 100 mL portions of ethanol and two 100 mL portions of water and dried at 37° C. under reduced pressure to obtain 30.9 g (65 percent of theory from 2-ethoxy-4,6-difluoropyrimidine) of the title compound as a light tan solid of 90 percent purity.

19. Preparation of 2-Chlorosulfonyl-5-ethoxy-7-fluoro[ 1,2,4]triazolo[1,5-c]pyrimidine From 2,2'-Dithiobis(5-ethoxy-7-fluoro[1,2,4]triazolo[1,5-c]pyrimidine)

A mixture containing 53.3 g of 88 percent purity (0.11 mol) of 2,2'-dithiobis(5-ethoxy-7-fluoro[ 1,2,4]triazolo[1,5-c]pyrimidine), 483 g of dichloromethane, and 12.0 g of water was prepared and cooled to about 5° C. Chlorine (42.5 g, 0.60 mol) was sparged into this mixture with cooling and stirring over a 2.5-hour period so that the temperature did not rise above about 15° C. Another 37.1 g of water was added during the course of the chlorine addition. The solids originally present became thicker at first and then essentially everything went into solution. The resulting mixture was diluted with about 200 mL of water and the phases were separated. The gold colored organic phase was washed with three 400 mL portions of water, dried over magnesium sulfate, filtered, and concentrated by evaporation under reduced pressure with a bath temperature up to 38° C. The title compound was contained in the residue, which amounted to 59.5 g (96 percent of theory) and was a waxy yellow-gold solid. A 12.66 g portion of this was purified by dissolving it in about 30 mL of dichloromethane, adding about 30 mL of hexane, and cooling. The precipitate that formed was recovered by filtration, dried to obtain 8.15 g of the title compound as a white solid. A 3.16 g second crop was also obtained. The product was identified spectroscopically to be the same compound as that reported in U.S. Pat. No. 5,163,995.

20. Preparation of 2-chlorosulfonyl-5-ethoxy-7-fluoro[ 2,4]triazolo[1,5-c]pyrimidine From 5-Ethoxy-7-fluoro[ 1,2,4]triazolo[1,5-c]pyrimidine-2(3H)-thione A mixture consisting of 3.7 g (17.3 mmol) of 5-ethoxy-7-fluoro[1,2,4]triazolo[1,5-c]pyrimidine-2(3H)-thione, 45 mL of dichloromethane, and 15 mL of water was placed in a three necked flask equipped with a mechanical stirrer, an outlet tube connected to a caustic scrubber, a chlorine inlet sparge tube, and a cooling bath. Compete solution was not attained. Chlorine was sparged into the solution at 0° C. with stirring and cooling until 7.0 g, (99 mmol) was added. The solids all dissolved. The aqueous and organic layers were separated and the organic layer was dried over magnesium sulfate and concentrated by evaporation under reduced pressure to obtain the title compound as a residue. The recovered product, which was an orange solid of approximately 88 percent purity, amounted to 3.6 g (75 percent of theory). The compound was identified spectroscopically to be the same as that reported in U.S. Pat. No. 5,163,995.

What is claimed is:

1. A 5-alkoxy-1,2,4-triazolo-pyrimidine- 3(2H)-thione compound of the formula:

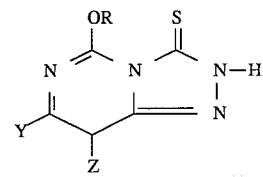

wherein
one of Y and Z represents F, Cl, Br, R', or OR' and the other represents H; and R and R' each independently represents $CH_3$ or $C_2H_5$ and the trialkylammonium salts thereof which are adducts of said compound and a trialkylamine-compound having three to twenty-one carbon atoms and a pKa of about 9.4 to about 11.4.

2. A 5-alkoxy-1,2,4-triazolo[4,3-c]pyrimidine-3(2H)-thione compound according to claim 1.

3. A trialkylammonium salt of a 5-alkoxy 1,2,4-triazolo [4,3-c]pyrimidine-2(3H)-thione compound according to claim 1.

4. A salt according to claim 3 wherein the trialkylamine compound is a compound of the formula

wherein $R^1$, $R^2$, and $R^3$ each independently represents $C_1$–$C_4$ alkyl or benzyl or two of $R^1$, $R^2$, and $R^3$ together represent a moiety of the formula —$(CH_2)_4$—, —$(CH_2)_5$—, $O(C_2H_4$—$)_2$, or $CH_3N$ $(C_2H_4$—$)_2$ or all three of $R^1$, $R^2$, and $R^3$ together represent a moiety of the formula $N(C_2H_4$—$)_3$.

5. A salt according to claim 4 wherein the trialkylamine compound is triethylamine ($R^1$, $R^2$, and $R^3$ each represents $C_2H_5$).

6. A compound according to claim 1 wherein one of Y and Z represents Cl or F and the other represents H.

7. A compound according to claim 6 which is 5-ethoxy-7-fluoro-1,2,4-triazolo[4,3-c]pyrimidine-3(2H)-thione.

8. A compound according to claim 6 which is 8-fluoro-5-methoxy-1,2,4-triazolo[4,3-c]pyrimidine-3(2H)-thione.

9. A compound according to claim 6 which is 8-chloro-5-methoxy-1,2,4-triazolo[4,3-c]pyrimidine-3(2H)-thione.

10. A method of use of a 5-alkoxy-1,2,4-triazolo[ 4,3-c]pyrimidine-3(2H)-thione compound of the formula:

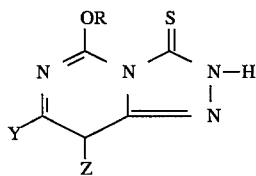

wherein
one of Y and z represents F, Cl, Br, R', or OR' and the other represents H; and R and R' each independently represents $CH_3$ or $C_2H_5$ which method consists essentially of treating said compound with between at least about one and about three molar equivalents of an alkali metal alkoxide of the formula ROM wherein R represents $CH_3$ or $C_2H_5$ and M represents an alkali metal in a medium containing an alcohol of the formula ROH wherein R represents $CH_3$ or $C_2H_5$, the alkali metal alkoxide and the alcohol selected so that R is the same in the alkali metal alkoxide, the alcohol, and the 5-alkoxy-1,2,4-triazolo[ 4,3,-c]pyrimidine-3(2H)-thione compound, at a temperature of about −10° C. to about 40° C., and thereafter acidifying the mixture to obtain a 5-alkoxy triazolo[ 1,5-c]pyrimidine-2(3H)-thione compound of the formula:

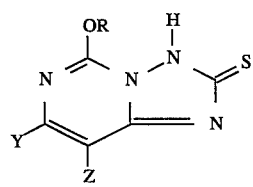

wherein R, Y, and Z are as defined before.

11. A method according to claim 10 wherein one of Y and Z represents Cl or F and the other represents H.

12. A method according to claim 10 wherein R represents ethyl.

13. A method according to claim 10 wherein the temperature is between about 0° C. and about 30° C.

14. A method according to claim 10 wherein the alkali metal is sodium.

15. A method according to claim 10 wherein the mole ratio of alkali metal alkoxide to 5-alkoxy-1,2,4-triazolo[4,3-c]pyrimidine-3(2H)-thione compound is between about 1.03 and 1.5.

16. A method according to claim 10 wherein the acidification is carried out with hydrochloric acid.

17. A method of use of a trialkylammonium salt of a 5-alkoxy-1,2,4-triazolo[4,3-c]pyrimidine-3(2H)-thione compound, which salt is an adduct of a compound of the formula:

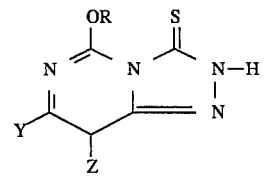

wherein
one of Y and Z represents F, Cl, Br, R', or OR' and the other represents H; and R and R' each independently represents $CH_3$ or $C_2H_5$ and a trialkylamine compound having a pKa of about 9.4 to about 11.4 which method consists essentially of treating said salt with at least about an equimolar amount of a benzyl halide or a $C_2$–$C_4$ alkyl halide in an inert solvent and obtaining a 3-hydrocarbylthio-5-alkoxy-1,2,4-triazolo[4,3-c]-pyrimidine compound of the formula:

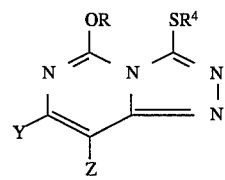

wherein X, Y, and R are defined as before and $R^4$ represents benzyl or $C_2$–$C_4$ alkyl.

18. A method according to claim 17 wherein one of Y and Z represents Cl or F and the other represents H.

19. A method according to claim 17 wherein $R^4$ represents benzyl.

20. A method according to claim 17 wherein the trialkylamine compound is a compound of the formula:

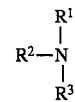

wherein $R^1$, $R^2$, and $R^3$ each independently represents $C_1$–$C_4$ alkyl or benzyl or two of $R^1$, $R^2$, and $R^3$ together represent a moiety of the formula —$(CH_2)_4$—, —$(CH_2)_5$—, $O(C_2H_4-)_2$, or $CH_3N(C_2H_4-)_2$ or all three of $R^1$, $R^2$, and $R^3$ together represent a moiety of the formula $N(C_2H_4-)_3$.

21. A method according to claim 20 wherein the trialkylamine compound is triethylamine.

22. A method according to claim 17 wherein R represents methyl.

23. A method according to claim 17 wherein the solvent is methanol when R represents methyl and is ethanol when R represents ethyl.

* * * * *

UNITED STATES PATENT AND TRADEMARK OFFICE
CERTIFICATE OF CORRECTION

PATENT NO.   : 5,480,991
DATED        : JAN. 2, 1996
INVENTOR(S)  : JON A. ORVIK; DAWN SHIANG

It is certified that error appears in the above-indentified patent and that said Letters Patent is hereby corrected as shown below:

COVER PAGE, INCORRECT TITLE, "2-ALKOXY-4-HYDROAZINOPIMIDINE
                              COMPOUNDS AND THEIR USE IN THE
                              PREPARATION OF
                              5-ALKOXY-1,2,4-TRIAZOLO[4,3-C]
                              PYRIMIDINE-3(2H)-THIONE COMPOUNDS

Should read

5-ALKOXY-1,2,4-TRIAZOLO[4,3-C]PYRIMIDINE-3(2H)-THIONE COMPOUNDS AND THEIR USE IN THE PREPARATION OF 5-ALKOXY[1,2,4] TRIAZOLO [1,5-C]PYRIMIDINE-2(3-H)-THIONE AND 3-HYDROCARBYLTHIO-5-ALKOXY-1,2,4-TRIAZOLO [4,3-C]PYRIMIDINE COMPOUNDS.

Signed and Sealed this

Thirtieth Day of July, 1996

Attest:

BRUCE LEHMAN

Attesting Officer        Commissioner of Patents and Trademarks